(12) United States Patent
Melin et al.

(10) Patent No.: US 8,822,231 B2
(45) Date of Patent: Sep. 2, 2014

(54) ASSAY METHOD AND DEVICE

(75) Inventors: Jonas Melin, Uppsala (SE); Christina Jönsson, Gnesta (SE)

(73) Assignee: Johnson & Johnson AB (SE)

( * ) Notice: Subject to any disclaimer, the term of this patent is extended or adjusted under 35 U.S.C. 154(b) by 766 days.

(21) Appl. No.: 12/988,162

(22) PCT Filed: Apr. 14, 2009

(86) PCT No.: PCT/SE2009/050380
§ 371 (c)(1),
(2), (4) Date: Jan. 25, 2011

(87) PCT Pub. No.: WO2009/128774
PCT Pub. Date: Oct. 22, 2009

(65) Prior Publication Data
US 2011/0117674 A1 May 19, 2011

(30) Foreign Application Priority Data

Apr. 16, 2008 (SE) ...................................... 0800871

(51) Int. Cl.
*G01N 33/558* (2006.01)

(52) U.S. Cl.
USPC .......... 436/514; 422/400; 422/68.1; 436/501; 436/518; 436/524; 436/528; 436/164; 436/165; 436/172; 435/7.1; 435/283.1; 435/287.1; 435/287.2; 435/288.7

(58) Field of Classification Search
USPC ......... 422/400, 68.1; 436/501, 514, 518, 524, 436/528, 164, 165, 172; 435/7.1, 283.1, 435/287.1, 287.2, 288.7
See application file for complete search history.

(56) References Cited

U.S. PATENT DOCUMENTS

| | | | |
|---|---|---|---|
| 6,143,511 A | 11/2000 | Eyre | |
| 6,642,007 B1 | 11/2003 | Saltarelli et al. | |
| 7,271,009 B1 | 9/2007 | Watkins et al. | |
| 7,879,624 B2 * | 2/2011 | Sharrock | 436/518 |
| 2002/0004246 A1 * | 1/2002 | Daniels et al. | 436/514 |
| 2002/0037506 A1 | 3/2002 | Lin et al. | |
| 2003/0054571 A1 * | 3/2003 | Watkins et al. | 436/526 |
| 2004/0132122 A1 | 7/2004 | Banerjee et al. | |
| 2006/0239859 A1 * | 10/2006 | Ohman et al. | 422/100 |
| 2007/0190585 A1 | 8/2007 | Apel et al. | |

FOREIGN PATENT DOCUMENTS

| | | |
|---|---|---|
| CN | 101058651 A | 10/2007 |
| DE | 100 54 093 A1 | 5/2002 |
| EP | 1 327 886 A1 | 7/2003 |
| JP | 2006-201190 | 8/2006 |
| JP | 2007-530938 | 11/2007 |
| WO | WO 95/24649 | 9/1995 |
| WO | WO 98/32018 | 7/1998 |
| WO | WO 01/14880 A1 | 3/2001 |
| WO | WO 01/40306 A1 | 6/2001 |
| WO | WO 2005/089082 A2 | 9/2005 |
| WO | WO 2005/121798 A1 | 12/2005 |
| WO | WO 2006/137785 A1 | 12/2006 |
| WO | WO 2007/023372 A2 | 3/2007 |
| WO | WO 2007/054714 A2 | 5/2007 |

OTHER PUBLICATIONS

Supplementary European Search Report for EP Application No. 09 731 672.3; mailed Mar. 24, 2011; 8 pages.
Japanese Office Action for Japanese Application No. 2011-504963; dated Oct. 23, 2012 (4 pages).
Russian Office Action for Russian Application No. 2010146454; dated Jun. 27, 2013 (3 pages).
Chinese Office Action and Search Report for CN Application No. 200980122643.0; dated Feb. 12, 2014 (13 pages).
Enzyme Immunoassay Method; by: Jiang Jingan, People's Medical Publishing House; Published Mar. 31, 1984; 4 pages.
Biochemistry Experiment Techniques; by: Li Qiaozhi, China Light Industry Press; Published Feb. 28, 2007; 7 pages.
Expanding Assay Dynamics: A Combined Competitive and Direct Assay System for the Quantification of Proteins in Multiplexed Immunoassays; Michael Hartmann et al.; Clinical Chemistry (2008); vol. 54; No. 6; pp. 956-963.
International Search Report/ Written Opinion for PCT Application No. PCT/SE2009/050380; mailed Jul. 1, 2010; 16 pages.

* cited by examiner

*Primary Examiner* — Melanie Y Brown
(74) *Attorney, Agent, or Firm* — Hiscock & Barclay, LLP

(57) ABSTRACT

A method for the analysis of at least two analytes in a liquid sample, in which a substrate is provided wherein at least two different types of capturing molecules are immobilized on the substrate and wherein each type of capturing molecule has specific affinity for an analyte. The sample is contacted with capturing molecules, wherein for at least one analyte to be analyzed contact is induced between the capturing molecules and a labelled detection molecule with specific affinity for the analyte, and for at least one another analyte to be contact is induced between the capturing molecules and a labelled version of the analyte. A detectable signal is measured from the labelled detection molecule and the labelled analyte on the substrate, wherein the concentration of the labelled analyte is adapted to the concentration of the analyte in the sample.

13 Claims, 2 Drawing Sheets

ASSAY METHOD AND DEVICE

CROSS REFERENCE TO RELATED APPLICATIONS

Pursuant to 35 USC §371, this application is a National Stage of International Application No. PCT/SE2009/050380, filed Apr. 14, 2009, which claims priority to Swedish Patent Application No. SE 0800871-6, filed Apr. 16, 2008 under applicable paragraphs of 35 USC §119, wherein the entire contents of each above-noted document is herein incorporated by reference.

TECHNICAL FIELD OF THE INVENTION

The present invention concerns a method and an assay device for the analysis of liquid samples.

BACKGROUND OF THE INVENTION

In many assays, it is desired to measure the concentration of two or more analytes simultaneously in one sample. This is also the case in affinity-based assays, such as immunoassays. Often, the analytes are present in very different concentrations. This may be a problem for affinity-based assays when the concentration of the different analytes are to be measured simultaneously, since there is a risk that the signal resulting from the measurement of one analyte may saturate or affect the signal resulting from the other.

Saturation may occur in an affinity-based assay comprising capturing means for instance when all capturing sites are occupied. Saturation may also occur when a transducer, such as a sensor measuring fluorescence from labelled molecules, is saturated.

In the prior art there has been made efforts to solve the problem to measure two or more analytes with very different concentrations in affinity-based assays. One approach is to split the sample into several aliquots, which are diluted to different concentrations. Another approach is to adjust the gain of the transducer, detector or sensor to the different concentrations.

U.S. Pat. No. 7,271,009 discloses immunological assays for several biological markers in a sample comprising the use of particles. Each particle is coated with one type of molecules taking part in the affinity-based assay. There are several types of particles, each coated with one type of molecule. To handle situations where the levels of the various analytes differ considerably, the signal is lowered for some of the analytes by the use of a diluting agent. It is described that the diluting agent does not engage in the specific binding with any of the analytes. The diluting agent competes for the sites available on the particle and lowers the coating density of the analyte. The number of analyte molecules which are captured are thus reduced by using the diluent. There is also described an embodiment where some particles are coated with an agent which increases the sensitivity for a particular analyte.

In some analysis devices according to the state of the art, a capturing antibody or a capturing molecule captures one or more analytes. The binding of analytes to the capturing sites is interrupted before equilibrium before all capturing sites are saturated so that the signal shall not become too high.

In some situations there is only one binding epitope available on at least one the analytes to be detected.

Although techniques according to the prior art are used, there is room for an improvement regarding that the sample may have to be diluted in several steps in several aliquots and/or that the gain of the transducer, detector and/or sensor has to be adjusted to accommodate different concentration levels. It is also desired to have a quick assay with as few steps as possible, where for instance particles do not have to be handled. It is also desirable to have an assay in which no diluent has to be added. An assay where it is possible to measure at least one analyte with only one epitope is also desired. It is also desired to have an assay which is able to measure the concentration of an analyte with only one epitope in a liquid sample mixture.

SUMMARY OF THE INVENTION

One object of the present invention is to provide an improved method and a device for carrying out the method which obviates at least some of the drawbacks in the prior art.

Advantages of the method and device include that no splitting of the sample into several aliquots, which are diluted differently, has to be made.

Another advantage is that the gain of the transducer, detector and/or sensor does not have to be adjusted to take into account very different concentration levels.

A further advantage is that no diluent has to be added to the capturing molecules in an affinity based assay. Also no affinity enhancing additive has to be added.

Advantages also include that no particles have to be handled. The method is simple and easy to perform, since there are few steps to perform.

Another advantage is that the binding of analyte molecules to the capturing molecules can be performed until equilibrium is reached. Thus, the binding does not have to be stopped before equilibrium is reached in order not to saturate all capturing sites. This has the advantage that it is not necessary to stop the binding at a well defined time. One advantage is thus that it is possible to achieve high precision by reaching equilibrium. In the technique according to the prior art, it is difficult to stop the binding at exactly the same stage every time since it is difficult to control all parameters influencing the binding rate.

A further advantage is that it is possible to measure several analytes where at least one analyte has only one epitope to which an antibody can bind.

The manufacturing of the device is easy and cost efficient. The simplicity also makes the method very cost efficient.

In a first aspect there is provided a method for the analysis of at least two analytes in a liquid sample, said method comprising the steps of:

a) providing a substrate wherein at least two different types of capturing molecules are immobilized on the substrate and wherein each type of capturing molecule has specific affinity for an analyte, b) contacting the sample with said capturing molecules, c) for at least one analyte to be analysed: inducing contact between the capturing molecules and a labelled detection molecule with specific affinity for the analyte, and for at least one another analyte to be analyzed inducing contact between the capturing molecules and a labelled version of the analyte, and d) measuring a detectable signal from the labelled detection molecule and the labelled analyte on the substrate, wherein the concentration of the labelled analyte is adapted to the concentration of the analyte in the sample.

In a second aspect, there is provided a device suited for the method.

Further aspects and embodiments of the present invention are defined in the appended claims, which are incorporated herein by reference.

BRIEF DESCRIPTION OF THE DRAWINGS

The invention will be described in closer detail in the following description, examples, and attached drawings, in which.

DETAILED DESCRIPTION OF THE INVENTION

Definitions

Figure 1:
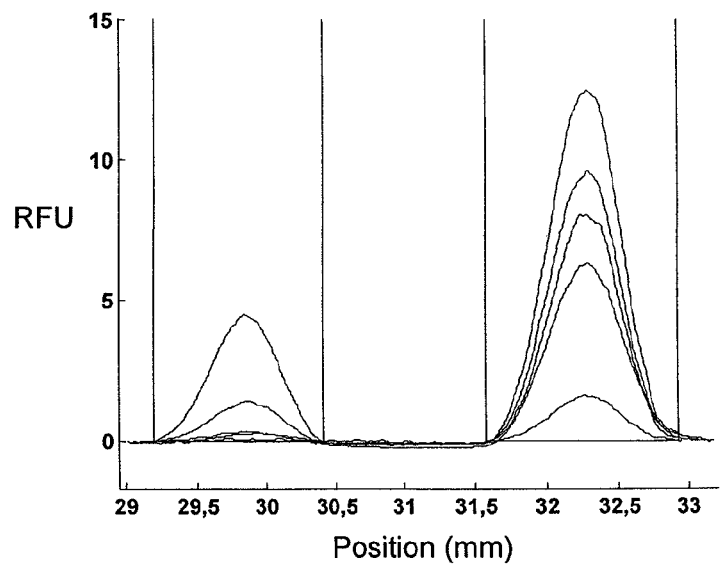
FIG. 1 shows the relative fluorescence intensity (RFU) as a function of position in a microfluidic channel.

Before the present method and device is described, it is to be understood that this invention is not limited to the particular configurations, method steps, and devices disclosed herein as such configurations, steps and devices may vary somewhat. It is also to be understood that the terminology employed herein is used for the purpose of describing particular embodiments only and is not intended to be limiting since the scope of the present invention will be limited only by the appended claims and equivalents thereof.

It must also be noted that, as used in this specification and the appended claims, the singular forms "a", "an", and "the" include plural referents unless the context clearly dictates otherwise. Thus, for example, reference to a reaction mixture containing "an antibody" includes a mixture of two or more antibodies.

In describing and claiming the present invention, the following terminology will be used in accordance with the definitions set out herein.

As used throughout the claims and the description, the term "about" when used in the context of numeric values denotes an interval of accuracy, familiar and acceptable to a person skilled in the art. Said interval is ±10%.

As used throughout the claims and the description, the term "analyte" means a substance or chemical or biological constituent of which one or more properties are determined in an analytical procedure. An analyte or a component itself can often not be measured, but a measurable property of the analyte can. For instance, it is possible to measure the glucose concentration.

As used throughout the claims and the description, the term "capturing molecule" means a molecule with the ability to bind to and capture an analyte molecule.

As used throughout the claims and the description, the term "detectable group" means any arrangement of molecules or atoms that can be detected when present on a substrate.

As used throughout the claims and the description, the term "detectable signal" means any signal that can be detected, including but not limited to electromagnetic waves, electrical signals, electrochemical signals, chemical signals, magnetic fields, radiological signals, and masstags.

As used throughout the claims and the description, the term "detection molecule" means a molecule with the ability to bind to an analyte and comprising a detectable group.

As used throughout the claims and the description, the term "labelled analyte" means an analyte comprising a detectable group.

As used throughout the claims and the description, the term "labelled detection molecule" means a detection molecule comprising a detectable group.

As used throughout the claims and the description, the term "sample" means a mixture or a solution to be analyzed.

Examples of samples include but are not limited to blood, plasma, serum, sweat, saliva, urine, lachrymal fluid, water samples, and suspensions or solutions of food samples.

As used throughout the claims and the description, the term "substrate" means a support on which molecules taking part in the analysis are supported.

In a first aspect there is provided a method for the analysis of at least two analytes in a liquid sample, said method comprising the steps of:

a) providing a substrate wherein at least two different types of capturing molecules are immobilized on the substrate and wherein each type of capturing molecule has specific affinity for an analyte, b) contacting the sample with said capturing molecules, c) for at least one analyte to be analyzed: inducing contact between the capturing molecules and a labelled detection molecule with specific affinity for the analyte, and for at least one another analyte to be analyzed: inducing contact between the capturing molecules and a labelled version of the analyte, and d) measuring a detectable signal from the labelled detection molecule and the labelled analyte on the substrate, wherein the concentration of the labelled analyte is adapted to the concentration of the analyte in the sample.

There is provided a substrate to which there are immobilized capturing molecules. In one embodiment, the capturing molecules are immobilized at distinct areas. In one embodiment, different areas have different immobilized types of capturing molecules. The capturing molecules have an affinity for an analyte to be analyzed. In one embodiment, each type of capturing molecule has an affinity for at least one analyte to be analyzed. In one embodiment, there is one type of capturing molecule for each of the analytes to be analysed. In one embodiment, one type of capturing molecule has specific affinity for one analyte. In one embodiment there are two different types of capturing molecules. In one embodiment there are two different types of capturing molecules immobilized to two distinct and separate areas on the substrate. In an alternative embodiment, different types of capturing molecules are immobilized to the same distinct area. In one embodiment, capturing molecules are immobilized to the same area and can be distinguished by the type of detectable groups used in the assay. In one embodiment, at least two different types of capturing molecules are immobilized on at least two different areas on the substrate.

In one embodiment, there is provided a substrate to which several types of capturing molecules have been immobilized. In one embodiment each type of capturing molecules is immobilized to at least one distinct area.

In one embodiment there are areas to which there are attached mixtures of more than one different types of capturing molecules.

Examples of capturing molecules include but are not limited to antibodies, aptamers, nucleic acid probes, and antibody fragments. Examples of nucleic acid probes include but are not limited to DNA, RNA and PNA. Examples of antibody fragments include but are not limited to Fab and scFv. In one embodiment the capturing molecules are antibodies. In another embodiment the capturing molecule is at least one molecule selected from an antibody, an aptamer, a nucleic acid probe, a DNA probe, a RNA probe, a PNA probe, an antibody fragment, a Fab fragment, and a scFv fragment. In a further embodiment each of said capturing molecules is independently selected from the group consisting of an antibody, an aptamer, a nucleic acid probe, a DNA probe, a RNA probe, a PNA probe, an antibody fragment, a Fab fragment, and a scFv fragment.

The sample is contacted with the capturing molecules so that analytes in the sample can bind to capturing molecules to which they have a specific affinity. In one embodiment, the sample is contacted with the capturing molecules by adding the sample to the substrate of the device. In one embodiment, the sample is contacted with the device. In one embodiment, the sample is contacted with the capturing molecules for a period of time, sufficiently long to reach equilibrium for the binding of analyte molecules to the capturing molecules. It is an advantage that the reaction can be allowed to proceed to equilibrium.

When the sample has been contacted with the capturing molecules, at least two different kinds of molecules are contacted with the capturing molecules. The kinds of molecules that are contacted with the capturing molecules are adapted to the analyte to be used and the assay. There is added at least one type of labelled detection molecule. The detection molecule has a specific affinity for the analyte and comprises a group which allows it to be detected by any means. There is further added at least one labelled analyte. As an alternative or in addition to a labelled analyte, there may be added a labelled fragment of an analyte, which fragment comprises an epitope with the ability to bind to the capturing molecule. A labelled analyte is an analyte comprising a detectable group.

Examples of detectable groups include but are not limited to fluorophores, radiolabels, masstags, bioluminescence groups, chemoluminescence groups, and electrochemical labels.

For an analyte expected to be present in the sample in a low concentration, there is added a labelled detection molecule. The labelled detection molecule binds to the analyte molecules which are bound to the capturing molecule. The labels allow a detection of the detection molecules. The detected signal is a function of the concentration of analyte. The detected signal increases with an increasing concentration of analyte. This is a sandwich assay.

For an analyte expected to be present in the sample in a high concentration, there is added a labelled analyte to the sample. The labelled analyte is an analyte comprising a detectable group. Alternatively or in addition, an analogue of an analyte can be added. The labelled analyte competes with the analyte for the binding sites on the capture molecules. The amount of labelled analyte is adapted to the concentration of analyte molecules in the sample. A person skilled in the art can in the light of this description perform routine experiments with different concentrations of labelled analyte at a given concentration of analyte molecules in the sample and thus determine a suitable amount of labelled analyte. After addition, the amount of captured analyte (labelled and unlabelled) approaches the equilibrium value. The ratio of captured labelled analyte and unlabelled analyte will reflect the ratio of these species in the sample. The detected signal is a function of the concentration of analyte. The detected signal decreases with an increasing concentration of analyte. This is a competitive assay.

The labelled detection molecule and the labelled analyte are in one embodiment added simultaneously to the substrate. In an alternative embodiment, they are added sequentially. In one embodiment, at least one labelled analyte is added first and thereafter at least one labelled detection molecule is added. In an alternative embodiment, at least one labelled detection molecule is added first and thereafter at least one labelled analyte is added.

In one embodiment, the labelled detection molecule and the labelled analyte are added to the substrate. In one embodiment, the labelled detection molecule is pre dispensed on the substrate. In one embodiment, the labelled analyte is pre dispensed on the substrate. In one embodiment, both the labelled detection molecule and the labelled analyte are pre dispensed on the substrate. In one embodiment, a labelled detection molecule and/or a labelled analyte are pre dispensed and a labelled detection molecule and/or a labelled analyte are added to the substrate.

In one embodiment, the contact between the capturing molecules and a labelled analyte is induced by first adding a labelled analyte to the sample and then contacting the sample with the capturing molecules. Thus, there is the possibility to mix the sample with at least one analyte to be analyzed and thereafter to add the sample to the device so that the sample including the analyte is brought into contact with the capturing molecules.

In one embodiment, the above-noted steps b) and c) are performed in one step.

A pre dispensed labelled detection molecule or a pre dispensed labelled analyte is, in one embodiment, made by applying a substance to the substrate and drying the substance so that a solvent evaporates. In one embodiment, the solvent is water. In that way, a pre dispensed dried substance is on the substrate. In one embodiment, at least one agent is added to the solvent. Examples of such additives include, but are not limited, to BSA (bovine serum albumin) and trehalose.

When the liquid sample is added, the pre dispensed substance/substances start to dissolve. In one embodiment, the device has the pre dispensed substance/substances upstream compared to the immobilized capturing molecules and the dissolved pre dispensed substance/substances can flow downstream and react at the areas of the capturing molecules.

In one embodiment, the device has a time gate which allows the liquid sample to contact the capturing molecules and after a period of time the pre dispensed substance/substances are dissolved and allowed to react with the analytes and capturing molecules. A microfluidic switch for stopping a liquid during a time interval is known from, for instance U.S. 2004/0206408, which is explicitly incorporated herein by reference in its entirety.

In one embodiment, the device is intended to be used to analyze the concentration of a first and a second analyte in a liquid sample. A first analyte is present in a low concentration and a second analyte is present in a high concentration. The first analyte is expected to be present in a low concentration and is analyzed using the sandwich assay. The second analyte is expected to be present in a high concentration and is analyzed using the competitive assay. To a first area on the substrate, there are immobilized capturing molecules with the ability to specifically bind the first analyte and to a second area on the substrate there are immobilized capturing molecules with the ability to specifically bind the second analyte. When the sample has been contacted with the capturing molecules, a labelled detection molecule with the ability to specifically bind to the first analyte is added. There is also added a labelled version of the second analyte. The labelled detection molecules and the labelled version of the analyte are detected after a period of time.

Examples of detection molecules include, but are not limited to antibodies, antibody fragments, Fab, scFv, aptamers, nucleic acid probes, DNA, RNA, and PNA. In one embodiment, the detection molecules are antibodies. In one embodiment, the detection molecule is at least one molecule selected from an antibody, an antibody fragment, a Fab fragment, a scFv fragment, an aptamer, a nucleic acid probe, a DNA probe, a RNA probe, and a PNA probe.

In one embodiment, the sample is contacted with the capturing molecules for a period of time sufficiently long to reach equilibrium for the binding of analyte molecules to the capturing molecules.

In one embodiment, a microfluidic device is used to perform the assay.

In one embodiment, a device comprising at least one channel is used. In one embodiment, a device comprising at least one channel with areas with immobilised capturing molecules is used. In one embodiment such a channel further comprises pre dispensed labelled analyte molecules and/or pre dispensed labelled detection molecules. The sample is added to the device and the sample flows along at least one channel to the capturing molecules and the pre dispensed substances.

In one embodiment, the substrate is at least partly covered by projections substantially vertical to its surface, and having a height (H1), diameter (D1) and reciprocal spacing (x1, y1) such, that lateral capillary flow of said liquid sample is achieved.

In one embodiment, the substrate comprises at least one sample addition zone, at least one receiving zone with the capacity to receive at least a part of the sample and at least one connecting zone establishing a fluid connection between the sample addition zone(s) and the receiving zone(s).

In one embodiment, a sample addition zone, a receiving zone and a zone connecting a sample addition zone and a receiving zone comprise projections substantially vertical to the substrate surface, having a height (H1), diameter (D1) and reciprocal spacing (x1, y1) such, that lateral capillary flow of said liquid sample is achieved.

In a second aspect there is provided an analysis device comprising a substrate, said substrate comprising at least one sample addition zone, at least one receiving zone with the capacity to receive at least a part of the sample and at least one connecting zone establishing a fluid connection between the sample addition zone(s) and the receiving zone(s), said zones being at least partly covered by projections substantially vertical to said surface, and having a height (H1), diameter (D1) and reciprocal spacing (x1, y1) such, that lateral capillary flow of said liquid sample is achieved, wherein said substrate comprises at least two different types of capturing molecules immobilized on the substrate and wherein each type of capturing molecule has a specific affinity for an analyte.

In one embodiment, the substrate further comprises at least one pre dispensed substance.

In one embodiment, the substrate comprises at least one pre dispensed labelled detection molecule.

In one embodiment, the substrate comprises at least one pre dispensed labelled analyte.

In one embodiment, said substrate comprises a pre dispensed labelled detection molecule and a pre dispensed labelled analyte.

In one embodiment, said substrate comprises at least one pre dispensed labelled detection molecule and at least one pre dispensed labelled analyte.

EXAMPLES

Example 1

Microfluidic chips were used as substrates which were injection molded in thermoplastics (Zeonor 1060R, Zeon, Japan), and oxidized in oxygen plasma. The oxidation took place during 6 minutes in a plasma chamber (400 Plasma System) at a working pressure of 0.26 mbar, 1000 W and with a flow of oxygen at 100 ml/min. The chips were immersed in a solution of 3 vol % APTES (Fluka) in 95% ethanol (Kemetyl, Sweden) for 2 hours. Curing took place over night at room temperature in air which allowed for crosslinking of the silane resulting in a stable amine functionalized surface. APTES coated surfaces were subsequently immersed in an oxidized 2% dextran solution (Dextran T40 (40 kDa), Pharmacosmos, Denmark) for 2 hours, rinsed in MilliQ-$H_2O$ and further oxidized in 30 mM $NaIO_4$ (Sigma Aldrich) for 2 hours.

The molded chips had one sample addition zone where sample can be added, one receiving zone with the capacity to receive at least a part of the sample, and one connecting zone establishing a fluid connection between the receiving zone with the sample addition zone. The connecting zone had areas with capturing antibodies centered on the middle of the device. The sample addition zone, the receiving zone and the connecting zone had projections vertical to the substrate surface with a height 70 μm, diameter 90 μm and spacing 50 μm so that lateral capillary flow was created when sample was added.

The device was used for 2-plexed measurement of c-reactive protein (CRP) and NTproBNP. The clinically relevant concentration range of CRP in serum is about 0.5-500 μg/ml whereas for NTproBNP it is 10-10000 pg/ml, i.e. a concentration difference of more that four orders of magnitude. To enable measurements of analytes with such a huge difference in concentration CRP was measured in a competitive format and NTproBNP in a sandwich format.

The concentrations of both analytes were determined simultaneously in the same liquid sample by first immobilizing capture antibodies for the two analytes at different positions in the connecting zone. Capture antibodies (monoclonal αCRP, and αNTproBNP) were spotted in two lines across the fluidic channel. The spotting solution contained 1 vol % trehalose (Sigma Aldrich), 50 mM $NaPO_4$ (pH 7.5, Sigma Aldrich) buffer and 0.5 mg/ml capture antibody. The mixture was spotted under humid conditions (relative humidity 75%) with a Nano-plotter NP 2.1 (Ge-Sim, Germany) across the fluidic channel, resulting in a ~0.5×2 mm band. The total deposited volume for each band was of 5.25 nl.

Assays were carried out by addition of 15 μl serum sample solution mixed with Alexa 647 labelled CRP (250 ng/ml) to the sample zone of the chip. The sample flowed through the connecting channel, thus bringing it into contact with the capture antibodies. When the entire sample droplet had migrated into the pillar array 5 μl Alexa 647 labeled detection antibody (20 μg/ml in serum, monoclonal αNTproBNP, directed towards a different epitope than the capture antibody) was added to the sample zone. Finally, 15 μl serum was added to the sample zone as a washing step. The fluorescence signal intensity along the microfluidic connecting channel was recorded using a line illuminating fluorescence scanner, showing distinct peaks there capture antibodies had been deposited. FIG. 1 shows the relative fluorescence intensity (RFU) as a function of position in the microfluidic channel. Each line indicates the fluorescence signal recorded on one chip. The vertical lines indicate integration boundaries. A new chip was used for each assay.

Figure 2:
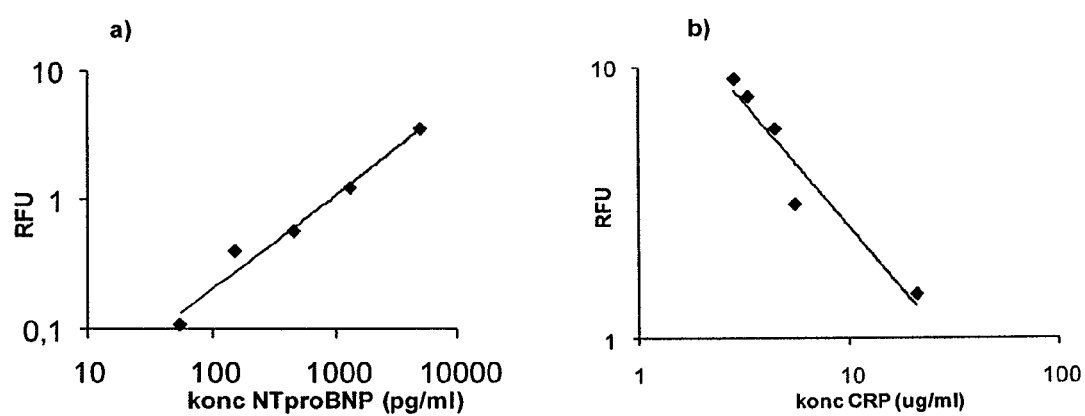
FIGS. 2a and b show assay results for NTproBNP and CRP respectively.

The procedure was repeated for five patient serum samples with known NTproBNP and CRP concentrations, as determined by the central laboratory at Uppsala University Hospital, Sweden. The peaks in the achieved intensity profiles were integrated and plotted as a function of the concentration measured by the central laboratory, see FIGS. 2a and 2b. The assay for NTproBNP exhibits a linear signal response to analyte concentration (FIG. 2a) whereas the signal for CRP is decreasing with analyte concentration (FIG. 2b). The highest CRP concentration (21 µg/ml) is more than 380000 times greater than the lowest NTproBNP (55 pg/ml).

Example 2

The experiment of example 1 was repeated, but this time assaying the combination of cardiac troponin I (cTnI) and CRP. Chips and assays were prepared and carried out in the same way as described for example 1, with the modification of using monoclonal αcTnI for cTnI capture and detection. CRP was measured in a competitive format and cTnI in a sandwich format. Serum samples were prepared by spiking CRP depleted serum with known concentrations of CRP and cTnI. Five samples with constant concentration of CRP (5 µg/ml) and increasing concentration of cTnI (0, 2, 10, 50, 250 ng/ml) were prepared and assayed.

Figure 3:
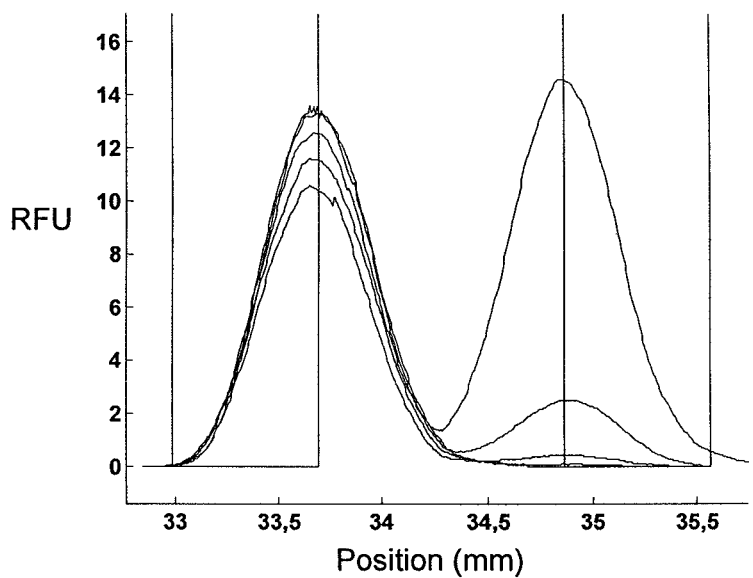
FIG. 3 shows the relative fluorescence intensity (RFU) as a function of position in another microfluidic channel.
Figure 4:
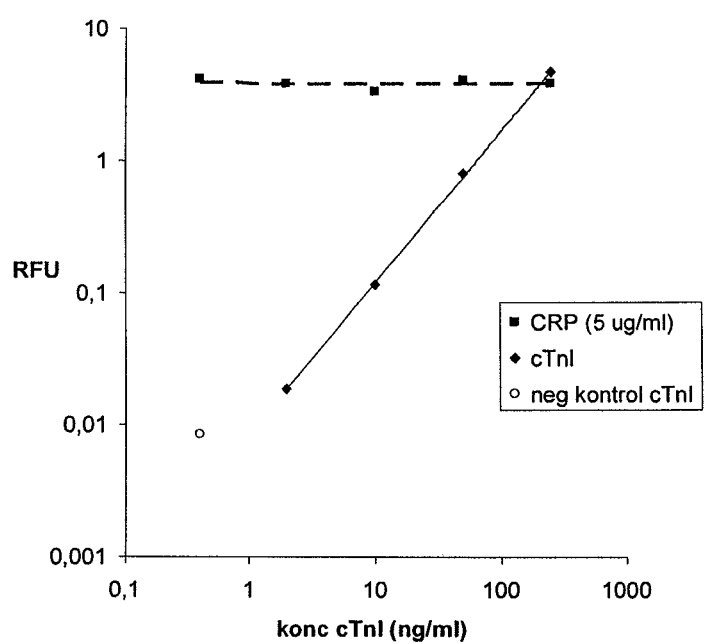
FIG. 4 shows assay results for cTnI and CRP.

FIG. 3 shows the relative fluorescence intensity (RFU) as a function of position in the microfluidic channel. The integrated peaks were plotted as a function of concentration as described in example 1. The assay for cTnI exhibits a linear signal response to analyte concentration (FIG. 4) whereas the signal for CRP is constant. The CRP signal is not affected by the variations in cTnI signal.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

The invention claimed is:

1. A method for analysis of at least two analytes in a liquid sample, including a first analyte expected to be in a first concentration and a second analyte expected to be in a second concentration that is much higher than the first concentration, said method comprising the steps of:
providing an analysis device comprising a substrate wherein at least two different types of capturing molecules are immobilized on the substrate in separately distinct areas and wherein each type of capturing molecule has specific affinity for the first and second analytes, respectively,
contacting the liquid sample with said immobilized capturing molecules,
for the first analyte to be analyzed and expected to have the first concentration: adding at least one type of labeled detection molecule having a specific affinity for the first analyte to be analyzed and inducing contact between the first analyte which is bound to or will be bound to the capturing molecules and the at least one added labelled detection molecule, and
for the second analyte to be analyzed and expected to have the second concentration: adding a labeled version or a labeled fragment of the second analyte and inducing contact between the capturing molecules, the second analyte, and the labelled version of the second analyte, and
measuring a detectable signal from each of: i) labelled detection molecules, which detection molecules are bound to the first analyte, which first analyte are bound to capturing molecules, which capturing molecules are bound to the substrate and in which the detectable signal increases with an increasing concentration of the first analyte, and ii) the labelled second analyte on the substrate in which the detectable signal decreases with an increasing concentration of the second analyte to be analyzed, wherein the concentration of the labelled analyte is adapted to the concentration of the unlabelled analyte in the liquid sample.

2. The method according to claim 1, wherein each of said capturing molecules independently is selected from the group consisting of an antibody, an aptamer, a nucleic acid probe, a DNA probe, a RNA probe, a PNA probe, an antibody fragment, a Fab fragment, and a scFv fragment.

3. The method according to claim 1, wherein said capturing molecules are antibodies.

4. The method according to claim 1, wherein said detection molecule is at least one molecule selected from an antibody, an antibody fragment, a Fab fragment, a scFv fragment, an aptamer, a nucleic acid probe, a DNA probe, a RNA probe, and a PNA probe.

5. The method according to claim 1, wherein said detection molecules are antibodies.

6. The method according to claim 1, wherein said contact between the capturing molecules and a labelled detection molecule is induced by adding a labelled detection molecule to the device.

7. The method according to claim 1, wherein said contact between the capturing molecules and a labelled detection molecule is induced by dissolution of a pre dispensed substance on the device.

8. The method according to claim 1, wherein said contact between the capturing molecules and a labelled analyte is induced by adding a labelled analyte to the device.

9. The method according to claim 1, wherein said contact between the capturing molecules and a labelled analyte is induced by the steps of first adding a labelled analyte to the sample and then contacting the sample with the capturing molecules.

10. The method according to claim 1, wherein said contact between the capturing molecules and a labelled analyte is induced by dissolution of a pre dispensed substance on the device.

11. The method according to claim 1, wherein the sample is contacted with the capturing molecules for a period of time sufficiently long to reach equilibrium for the binding of analyte molecules to the capturing molecules.

12. The method according to claim 1, wherein said substrate at least partly includes a plurality of projections substantially vertical to a support surface, said projections having a height (H1), diameter (D1) and reciprocal spacing (x1,y1) such, that lateral capillary flow of said liquid sample is achieved.

13. The method according to claim 1, wherein said substrate comprises at least one sample addition zone, at least one receiving zone with the capacity to receive at least a part of the sample and at least one connecting zone establishing a fluid connection between the sample addition zone and the at least one receiving zone.

* * * * *